(12) United States Patent
Raje et al.

(10) Patent No.: US 11,026,832 B2
(45) Date of Patent: Jun. 8, 2021

(54) INTRAUTERINE DEVICE WITH A RESTRICTED UPWARD MOVEMENT OF A STRING

(71) Applicant: PREGNA INTERNATIONAL LIMITED, Maharashtra (IN)

(72) Inventors: Ajit Raje, Maharashtra (IN); Usha Kumar, London (GB)

(73) Assignee: Pregna International Limited, Mumbai (IN)

( * ) Notice: Subject to any disclaimer, the term of this patent is extended or adjusted under 35 U.S.C. 154(b) by 475 days.

(21) Appl. No.: 15/576,362

(22) PCT Filed: Jul. 16, 2015

(86) PCT No.: PCT/IN2015/000286
§ 371 (c)(1),
(2) Date: Nov. 22, 2017

(87) PCT Pub. No.: WO2016/193987
PCT Pub. Date: Dec. 8, 2016

(65) Prior Publication Data
US 2018/0147085 A1  May 31, 2018

(30) Foreign Application Priority Data

May 30, 2015 (IN) .......................... 2100/MUM/2015

(51) Int. Cl.
*A61F 6/18* (2006.01)
*A61F 6/14* (2006.01)

(52) U.S. Cl.
CPC ................ *A61F 6/18* (2013.01); *A61F 6/144* (2013.01)

(58) Field of Classification Search
CPC .. A61K 9/0039; A61K 9/0036; A61K 9/0092; A61F 6/14; A61F 6/144; A61F 6/142; A61F 6/146; A61F 6/16; A61F 6/18; A61F 6/22; A61F 6/00; A61F 6/06; A61F 6/08; A61F 13/34
USPC ....... 128/830, 832, 833, 836, 839, 840, 831, 128/838
See application file for complete search history.

(56) References Cited

U.S. PATENT DOCUMENTS

| 2,122,579 | A | * | 7/1938 | Meckstroth | A61F 6/142 |
|---|---|---|---|---|---|
| | | | | | 128/839 |
| 3,507,274 | A | * | 4/1970 | Soichet | A61F 6/144 |
| | | | | | 128/840 |
| 3,902,483 | A | * | 9/1975 | Place | A61F 6/144 |
| | | | | | 128/839 |

(Continued)

FOREIGN PATENT DOCUMENTS

WO  WO-2007075086 A1 * 7/2007  ............... A61F 6/18

*Primary Examiner* — Alireza Nia
*Assistant Examiner* — Robin Han

(57) ABSTRACT

An intrauterine device (IUD) with a restricted movement of a string(s), the strings can be either a single string or two or more strings or a filament, emerging from the spherical bulge of IUD. The strings of IUD are of a differential strength so that the strings are soft and the hanging portion of the strings, "feelable" in the vaginal cavity, does not cause discomfort to the woman, nor bruise the organ of the partner during intercourse, at the same time the strings in the endocervical canal are relatively stiffer and not have the tendency to get curled up progressively. The strings optionally have marks to facilitate cutting by a surgeon to an accurate length.

14 Claims, 20 Drawing Sheets

(56) References Cited

U.S. PATENT DOCUMENTS

| | | | | |
|---|---|---|---|---|
| 3,993,057 A | * | 11/1976 | Ramwell | A61F 6/144 |
| | | | | 128/833 |
| 5,234,437 A | * | 8/1993 | Sepetka | A61B 17/12022 |
| | | | | 600/585 |
| 2008/0216842 A1 | * | 9/2008 | Acedo | A61F 6/144 |
| | | | | 128/839 |

* cited by examiner

Figure 1A   Figure 1B

INTRAUTERINE DEVICE WITH A RESTRICTED UPWARD MOVEMENT OF A STRING

FIELD OF THE INVENTION

This invention relates to the intrauterine device (IUD) and particularly to an IUD with one or more strings. More particularly, the invention relates to preventing curling up and retraction of the string(s) of the IUD in uterus.

BACKGROUND OF THE INVENTION

An intrauterine device (IUD) is a birth control device, which is placed in the uterus of a woman. IUDs have been known since several decades, and are popularly known as "Copper-T". IUDs are of different types viz. copper IUD, hormonal IUD, et cetera and are available in various shapes, for example T-shaped; and sized to fit inside uterus of women.

IUDs currently in the market are generally provided with one or more strings extending from the bottom of the IUD. When IUD is placed in uterus, the string(s) extend through the cervix and remain positioned in the vaginal cavity, such that a woman can "feel" the presence of string(s) with her finger.

IUD being a foreign matter in the body, there are possibilities that the IUD gets expelled from the uterus/body of the woman. Expulsions can happen anytime in the menstrual cycle (menstrual cycle is defined as duration from a start of one period to the start of the next period), more so during a heavy period. The causes of all expulsions are not exactly known, and expulsions are known to occur even if the period is not heavy. Nulliparous women, women with uterine abnormalities, fibroids are known to expel IUDs more commonly than others.

Women are advised to "feel" the presence of the string(s) by touching the string(s) with their finger after each menstrual period or at regular intervals of weeks, so as to be assured of presence of the contraceptive device. String(s) are also helpful for pulling the IUD out of the uterus when the IUD is required to be removed. Patent US3902483 describes an intrauterine device having two threads, a locator thread and a reserve thread. If women do not find the string, it makes them anxious that IUD has possibly got expelled and they are without protection from pregnancy.

Besides IUD getting expelled, there are many possible reasons for string not in place. One of the reasons that has relatively lately come to the knowledge is that strings are not in place although the IUD is in situ, that is, in the uterine cavity; because—the strings are curled up and retracted into the endocervical canal or uterine cavity. Patent US4372302 and US4561433 recognize this problem and describe instruments for retrieval of the retracted threads or strings of the IUD. These patents, however, do not address the cause and solution of the problem of curling/retracting.

Patent Publication Number EP0179518A1 describes an IUD extractor thread where an IUD is provided with an extractor thread and such thread is coated with metallic silver which helps in preventing the bacteriological infections which occur due to the normal threads of IUD. Although this invention deals with the IUD threads, but does not address curling.

Patent Publication Number US2011/0247630 describes an intrauterine device with string divided into upper, intermediate and lower portion. The upper portion is configured to attach the stem of IUD. Intermediate portion runs through endocervical canal and lower portion follows the contour of cervix. The disclosure is silent about string curling. The lower portion comprising a curved portion is configured to follow a contour of the external orifice of the cervix; and therefore, this method may prevent up curling of string, however, the procedure is painful, complex and intervening with active life of the women and her partner; and therefore is impractical.

One of the common ways to attach the string to the IUD frame is by having a through hole at the lower end of the IUD frame and tying the string by way of a knot. Patent application Number US2013/0298361A1 describes the knotting method. This disclosure is more towards achieving productivity rather than addressing said problem.

As can be easily appreciated, there is no prior invention which addresses the problem related to curling or retraction of strings.

Our invention addresses the cause of curling and or retracting of knotted strings and solves this problem.

OBJECTIVE OF THE INVENTION

The objective of the invention is to provide an intrauterine device wherein the string does not retract into the uterus through the endocervical canal of the female.

Another objective of the invention is to provide an intra-uterine device which is not unduly different in construction than current devices.

Yet another objective is to invent an intrauterine device with ease of manufacturing and the end product being economical.

Yet another objective of the invention is to provide an intrauterine device which is as hygienic, safe and proven for inserting in the uterus of the female as current devices.

SUMMARY OF THE INVENTION

Our invention deals with an intrauterine device with a restricted movement of a string. T-shaped IUD is considered for disclosure of our invention, however, the shape of the IUD is not a limitation and this invention pertains to IUDs of all shapes and type, whether copper or hormonal or medicinal.

An intrauterine device described here comprises of a central vertical stem having a pair of arms attached at a proximal end and a spherical bulge at a distal end. IUDs are provided with one or more strings which are attached to the stem either by knotting or by molding along with a frame of the IUD. String(s) emerge from the spherical bulge leaving the hanging portion of the string(s) freely suspended. The strings are soft and therefore can easily develop a tendency to curl/bend. These string(s) serve the purpose of ensuring presence of IUD, and removal of the IUD.

The present invention recognizes that the string(s) is required to be of differential strength so that it meets following requirements:

Requirement ONE: The string(s) ought to be soft, and hanging portion of the string(s) "feelable" in the vaginal cavity, should not cause discomfort to the woman, nor bruise the organ of the partner during an intercourse.

Requirement TWO: The string(s) reaching the internal cervical os ought to be relatively stiffer and not have the tendency to get curled up progressively.

Consequent to the contracting and relaxing muscular activities of the uterus, the string(s) gets gradually pulled or slid from the endocervical canal, thereby curling up in the uterus. Commonly available IUDs comprise of a single or two strings, emerging from the spherical bulge. An intrauterine device or an IUD as per this invention prevents a curling and retraction of the string(s) in the uterus by enhanced stiffness for the limited and specific length, termed as predetermined length.

According to this invention, an enhanced stiffness is achieved by unifying the strings. The unification, which essentially means combination of multiple strings is by any of the several methods, namely, by fusing two or more strings or, by coiling/wrapping one or more string over another or, by interweaving two or more strings with each other or, by two or more strings glued together to form a thicker string or, by knots tied at the regular intervals or, by twisting two or more strings together to form the strings with thicker diameter. In the IUD with a single string, a desired stiffness is achieved by thickening the string either in the form of a continuously varying thickness, or graded thickness, also termed as stepped thickness. The desired stiffness is also achieved by providing an envelope around the string(s). The desired stiffness is also attained by use of a filament as a string, which is made of extra soft material (thus value of modulus of elasticity E is low) and has relatively much larger area of cross-section, so that the product of area of cross section A and modulus of elasticity E is increased. String is optionally provided with a plurality of identification by way of a mark, whether formed during manufacturing of the string or subsequently by an additional process, at measured intervals. Such identification aids the surgeon in cutting a right length of the string or the filament after leaving a recommended length of string of about 2 to 3 cm in the vaginal cavity.

DESCRIPTION OF DRAWINGS

FIG. 12 shows a preferred embodiment whereby an envelope is provided around the string, while

FIG. 13 shows another embodiment whereby an envelope is provided around the string, while

FIG. 14 shows another embodiment whereby an envelope is provided around the string, while

DETAILED DESCRIPTION OF THE INVENTION

Preferred embodiment of the intra-uterine device (IUD) with a restricted movement of a string according to present invention will now be described in detail, with reference to the accompanying drawings. The terms and expressions which have been used here are merely for description and not for limitation. A "T-shaped" IUD is considered for illustration of our invention, however, the shape of the IUD is not a limitation and this invention pertains to IUDs of all shapes and type, whether copper/silver-copper or hormonal or medicinal.

Figure 1:
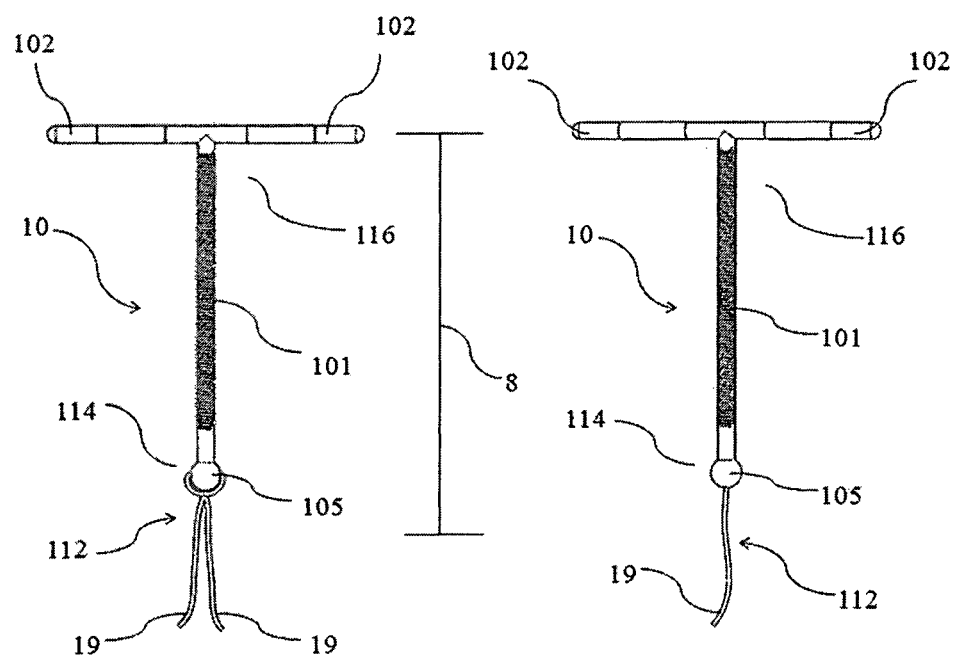
FIG. 1A and FIG. 1B show prior art IUDs with one or more than one string.
Figure 3:
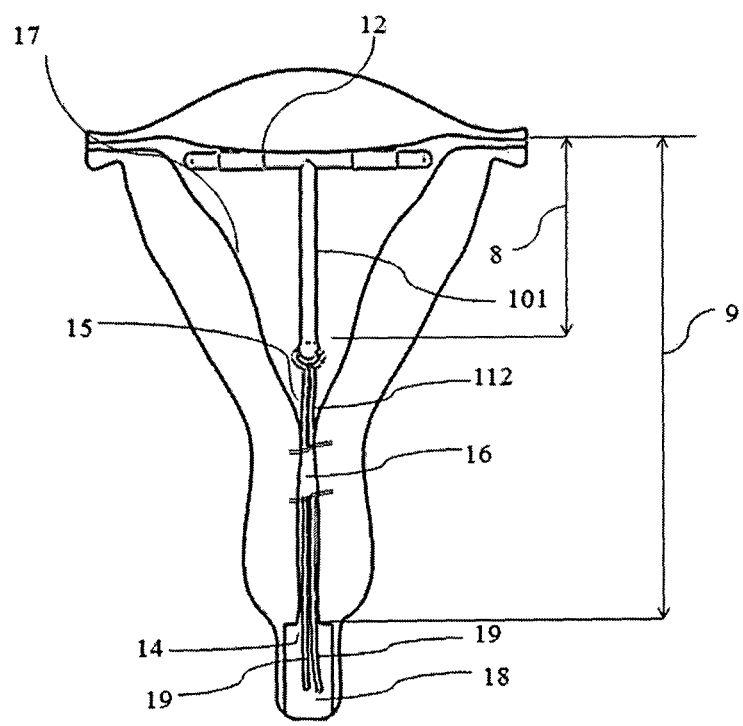
FIG. 3 shows position of different parts of IUD and string in the uterus, endocervical canal and vaginal cavity.

The known IUDs are provided with one or more strings. The string(s) is attached to the stem either by knotting or by molding along with a frame of the IUD. The strings are soft and therefore can easily develop a tendency to curl/bend. FIG. 1A showing a prior art intrauterine device (10) or IUD (10) comprises a central vertical stem (101) having a pair of arms (102) attached on a proximal end (116) of the central vertical stem (101), and a spherical bulge (105) at a distal end (114) of the central vertical stem (101). The String(s) (112) emerge from the spherical bulge (105) leaving a hanging portion (19) of the string(s) (112) suspended freely. These string(s) (112) serve the purpose of ensuring presence of the IUD (10), and removal of the IUD (10). As shown in FIG. 3, When the IUD (10) is placed into the uterus (17); these string(s) (112) extend through the endocervical canal (16) and remain positioned in the vaginal cavity (18). FIG. 1B shows another prior art intrauterine device (10) having a single string (112) suspended freely.

Figure 2:
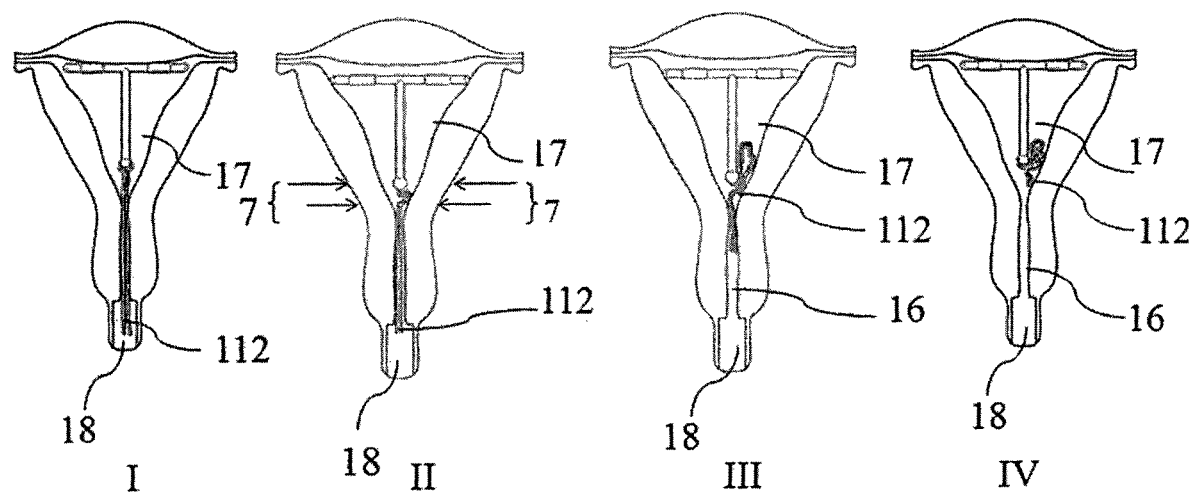
FIG. 2 illustrates how the progressive curling up of the strings occurs.

FIG. 2, read with earlier figures, shows how the string(s) (112) get curled up and "disappear" from the vaginal cavity (18). It is known that the IUDs (10) accommodate their position in the uterus (17) during the first few months after insertion. This movement of the IUD (10) inside the uterus (17) is most probably explained by contractility, as illustrated by arrows (7) of the uterine muscle (myometrium). During downward movement of the IUD (10) in the uterus (17), there is relative upward movement of the string(s) (112) against the central vertical stem (101) of the IUD (10) due to a differential stiffness of the central vertical stem (101) and a differential stiffness of the string(s) (112). It is easy to comprehend that the phenomenon of curling of string(s) (112) begins from a vicinity of a joint of the string(s) (112) with the spherical bulge (105) of the IUD (10). View-I, View-II, View-III and View-IV in FIG. 2 shows progressive curling up and retraction of the string(s) (112) into the endocervical canal (16) and gradually into the uterus (17).

As per present invention, the string(s) (112) is of a differential strength so that it meets following requirements:
Requirement ONE: The string(s) (112) ought to be soft, and the hanging portion (19) of the string(s) (112) "feelable" in the vaginal cavity (18), should not cause discomfort to the woman, nor bruise the organ of the partner during an intercourse.
Requirement TWO: The string(s) (112) reaching the internal cervical os (15) ought to be relatively stiffer and not have the tendency to get curled up progressively.

FIG. 3 shows an IUD (10) placed in a uterus (17) with the string(s) (112) emerging from the spherical bulge (105), the string(s) (112) running through the endocervical canal (16) and the hanging portions (19) of the string(s) (112) freely suspended in the vaginal cavity (18) such that the string(s) (112) can be felt by woman. A length (8) of the central vertical stem (101) of the IUD (10) is generally of an order of 29-36 mm and a distance (9) between a fundus (12) and an external cervical os (14) varies generally between 50 mm and 100 mm for different women depending on their age and other factors. In most women, a length of the endometrial cavity (distance from fundus to internal cervical os (15) is greater than a length of the commonly used IUDs. This implies that the spherical bulge (105) and a part of string(s) (112) remain above the internal cervical os (15).

It is known that consequent to the contracting and relaxing muscular activities of the uterus (17), the string(s) (112) gets gradually pulled or slid from the endocervical canal (16), thereby curling up in the uterus (17). Commonly available IUDs (10) comprise of a single or two strings (112), emerging from the spherical bulge (105) as shown in Figure-1B and Figure-1A respectively. An intra-uterine device or an IUD as per this invention prevents a curling and retraction of the string(s) (112) in the uterus (17) by an enhanced stiffness for a limited and specific length, termed as a predetermined length. The Stiffness can be arithmetically understood by the equation:

k=AE/L where k=stiffness

A=area of cross-section

E=modulus of elasticity of the material

L=length

Hence, it is clear that stiffness is directly proportional to the cross-section, or k αA(where α is the sign of proportionality)

Figure 4:
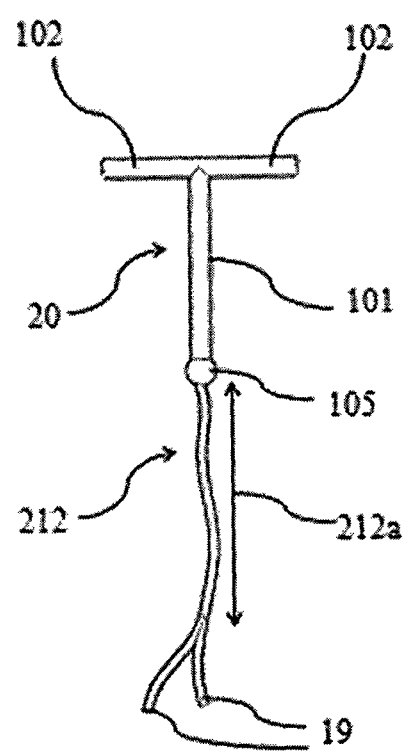
FIG. 4 shows a preferred embodiment of unification of strings.

According to this invention, described with FIG. 4 onwards, in an IUD (20) with two or more strings, an enhanced stiffness is achieved by unifying the strings. The unification, which essentially means combination of multiple strings is by any of the several methods, namely, by fusing two or more strings or, by coiling/wrapping one or more string over another or, by interweaving two or more strings with each other or, by two or more strings glued together to form a thicker string or, by knots tied at the regular intervals or, by twisting two or more strings together to form the strings with thicker diameter. In the IUD (20) with a single string, a enhanced stiffness is achieved by thickening the string either in the form of a continuously varying thickness, or a graded thickness, also termed as a stepped thickness. The enhanced stiffness is also achieved by providing an envelope around the string(s). The enhanced stiffness is also attained by use of a filament as a string, which is made of extra soft material (thus value of modulus of elasticity E is low) and has relatively much larger area of cross-section, so that the product of area of cross section A and modulus of elasticity E is increased.

FIG. 4, shows an embodiment with an IUD (20) having two strings (212) emerging from the spherical bulge (105) leaving the hanging portion (19) of the strings (212) freely suspended. A unification of the two or more strings (212) emerging from the spherical bulge (105) is a fusion of the two or more strings (212) together from below the spherical bulge (105) for a pre-determined length, hereinafter termed as a projected length (212a). The string(s) (212) are unified by fusing them together, from below the spherical bulge (105), for the projected length (212a) of the string(s) (212). The projected length (212a) remains inside the endocervical canal (16). The fusing together provides the enhanced stiffness and rigidity to the string(s) (212).The hanging portion (19) of the string(s) (212) is freely suspended in the vaginal cavity (18). The fusing could be by an ultrasonic welding or any other process by which a thermoplastic material, with or without additives, of which the strings (212) are made are brought to soft and thus fusible state. In the fusible state, the string(s) (212) are held together under a compressive force, which causes the discrete strings of the thermoplastic material to unify. The Fusion increases an area of cross-section of said strings (212), thus provides a required strength without altering a functionality of the string(s) (212). The hanging portion (19) of the string(s) (212) is either fused or unfused.

Figure 5:
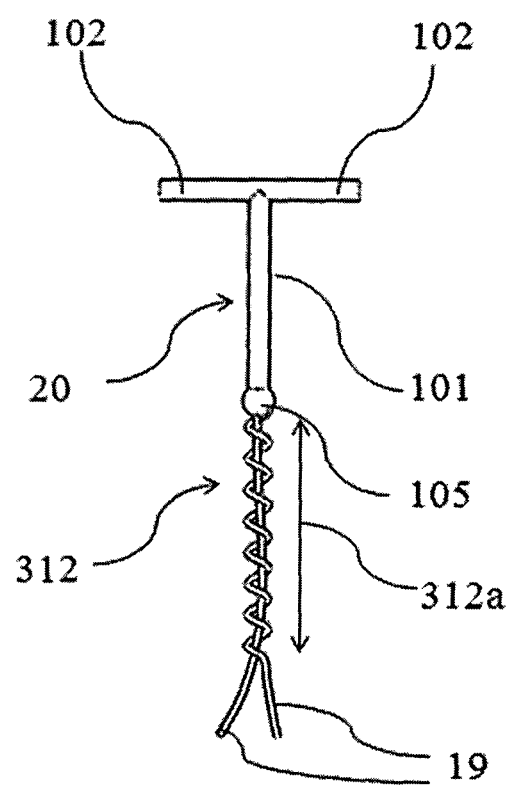
FIG. 5 shows another embodiment of unification of strings.

FIG. 5 shows another embodiment with the IUD (20) having two strings (312) emerging from the spherical bulge (105). A unification of the two or more strings (312) emerging from the spherical bulge (105) is a first string wrapped on a second string or a plurality of strings from below the spherical bulge for the projected length. To unify the strings (312), one of the two strings (312) is wrapped around on the other strings (312) from below the spherical bulge (105) to form the projected length (312a) of the string (312), which remains inside the endocervical canal (16). The wrapping of the first string over the second string or others increases an area of cross-section of said strings (312), thus provides the enhanced stiffness without altering a functionality of the strings (312).The hanging portion (19) of the strings (312) is suspended in the vaginal cavity (18).

Figure 6:
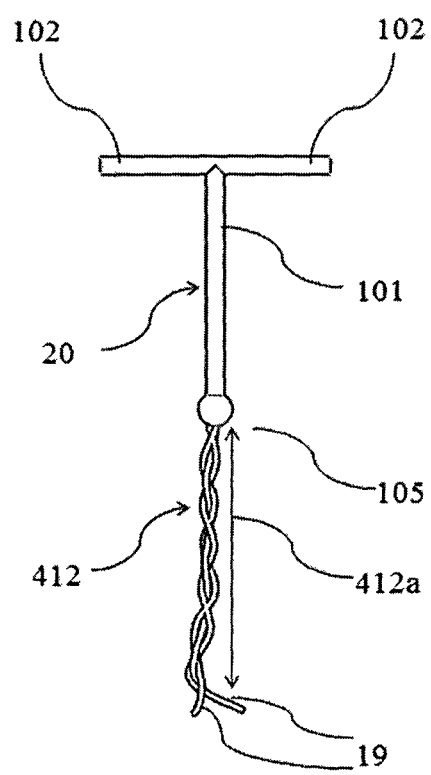
FIG. 6 shows yet another embodiment of unification of strings.

Another embodiment as shown in FIG. 6, the IUD (20) is having two or more strings (412) emerging from the spherical bulge (105). The unification of the two or more strings (412) emerging from the spherical bulge (105) is an interweave of the two or more strings (412) with one another to form a braid like structure below the spherical bulge for the projected length (412a). To unify the strings (412), the strings (412) are interwoven with one another to form the braid like structure below the spherical bulge (105) to form the projected length (412a) of the strings (412) which remains inside the endocervical canal (16). The Interweaving of the strings (412) together increases an area of cross section of said strings (412), thus provides the enhanced stiffness without altering a functionality of the strings (412). The hanging portion (19) of the strings (412) is suspended freely in the vaginal cavity (18).

Figure 7:
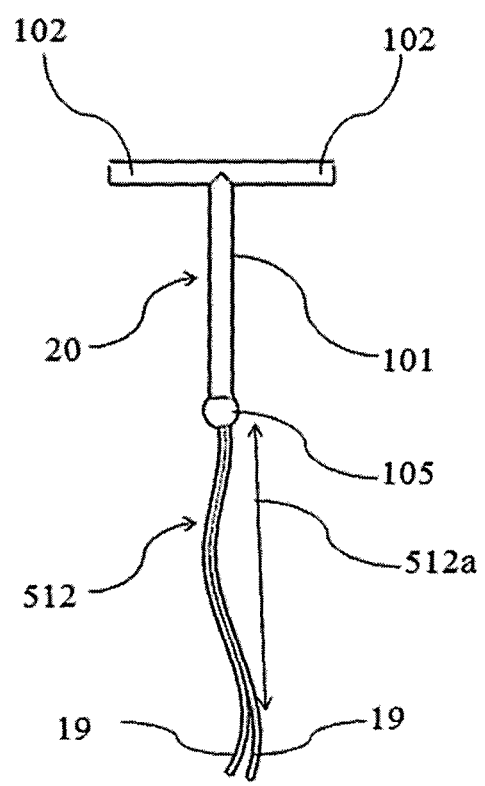
FIGS. 7, 8 and 9 show yet another embodiment of unification of strings.

As another embodiment shown in FIG. 7, the IUD (20) is having two strings (512) emerging from the spherical bulge (105). The unification of the two or more strings (512) emerging from the spherical bulge (105) is a glued portion of the two or more strings (512) together to form a string of a single thickness below the spherical bulge for the projected length (512a). To unify, the strings (512) are glued together below the spherical bulge (105) by use of an adhesive of medically approved grade to form the projected length (512a) of the strings (512). The Gluing of two or more strings (512) together increases an area of cross section of said strings (512), thus provides the enhanced stiffness without altering a functionality of the strings (512). The hanging portion (19) of two or more strings (512) is suspended freely in the vaginal cavity (18).

Figure 8:
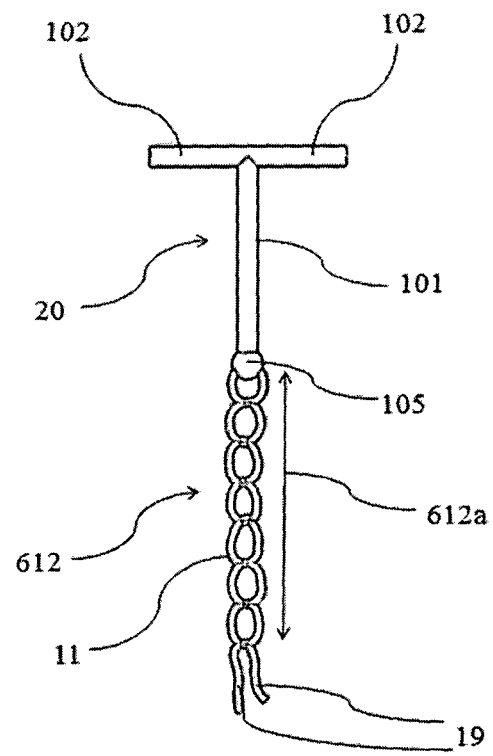

FIG. 8 shows another embodiment with IUD (20) having two or more strings (612) emerging from the spherical bulge (105). The unification of the two or more strings (612) is a division of the two or more strings (612) in nearly equally in two parts to form two set of said strings, said division of the two or more strings tied together by forming multiple knots at a regular intervals below the spherical bulge (105) for the projected length (612a). To unify, the number of strings are divided nearly equally in two parts so as to have only two set of said strings (612). The said strings (612) are tied together by forming multiple knots (11) at regular intervals below the spherical bulge (105) to form the projected length (612a) of two or more strings (612) in the endocervical canal (16). The Formation of multiple knots

(11) is analogous to a rope formation or any other mechanical entanglement of two or more strings (612). Such multiple knots (11) at the regular interval increase an area of cross section of said the strings (612), thus provides the enhanced stiffness without altering a functionality of said strings (612). The hanging portion (19) of two or more strings (612) is freely suspended in the vaginal cavity (18).

Figure 9:
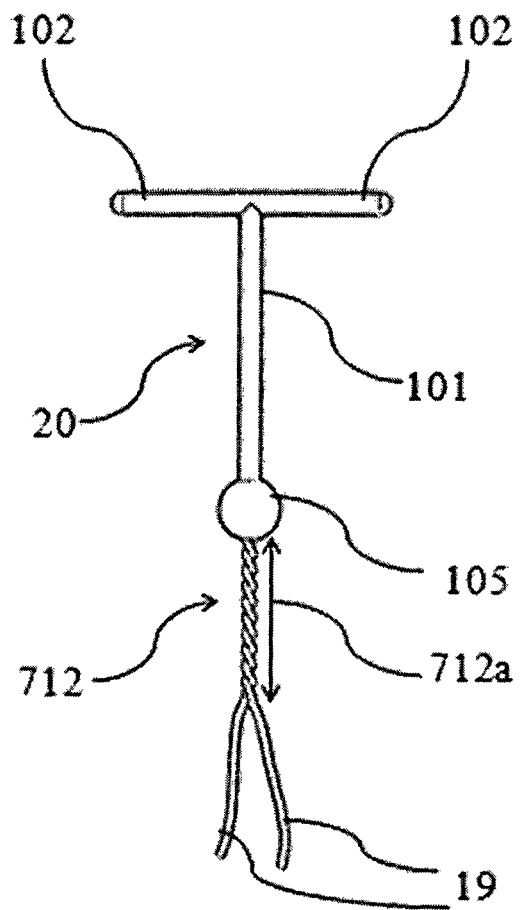

In another embodiment as shown in FIG. 9 with an IUD (20) having two or more strings (712) emerging from the spherical bulge (105) of IUD (20). The unification of the two or more strings (712) emerging from the spherical bulge (105) is a twist of the two or more strings (712) with one another below the spherical bulge (105) for the projected length (712a).To unify, the two or more strings (712) are twisted with each other below the spherical bulge (105) to form the projected length (712a) in the endocervial canal (16). Such twisting of two or more strings increases an area of cross section of said strings (712), thus provides the enhanced stiffness without altering a functionality of said strings (712). The hanging portion (19) of two or more strings (712) is freely suspended in the vaginal cavity (18).

Figure 10:
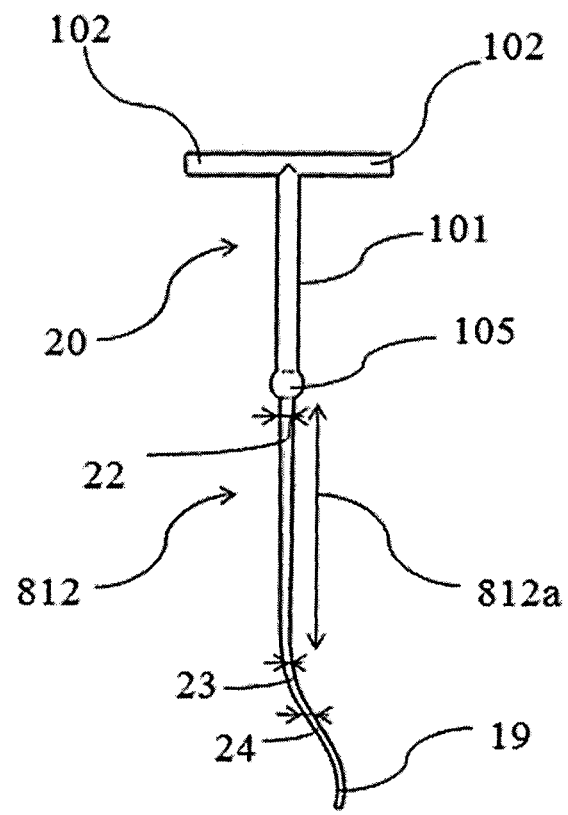
FIG. 10 and FIG. 11 show embodiments of this invention with single string.

According to this invention for IUD (20) with a single string (812), as shown in FIG. 10, the string (812) emerging from the spherical bulge (105) of the IUD (20), as a preferred embodiment, is of a progressively varying or a graded thickness below the spherical bulge (105) to from the projected length of said string (812a). A highest thickness (22) in a vicinity of the spherical bulge (105) is of the an order of one and a half times to three times a thickness of a prior art string and a minimum thickness (23), which is at the other end of the projected length (812a) is same as that of a prior art string. Such graded thickness of said string increases an area of cross section in the projected length (812a), thus provides the enhanced stiffness without altering a functionality of said strings (812). The hanging portion (19) of the string (812) is of an uniform thickness (24) and which is same as the minimum thickness (23) and is freely suspended in the vaginal cavity (18).

Figure 11:
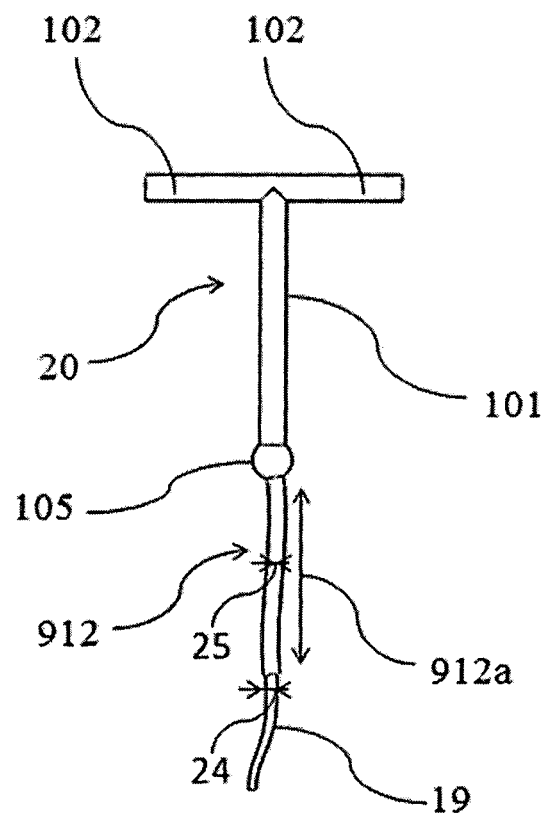

As another embodiment as shown in the FIG. 11, an IUD (20) having the single string (912) emerging from the spherical bulge (105) of IUD (20), has the string (912) of a stepped thickness (25) such that the thicker string forms the projected length (912a) of said string (912). The Stepped thickness (25) is of an order of one and a half times to three times a thickness/diameter of a prior art string. Such stepped thickness (25) increases an area of cross section in the projected length (912a), thus provides an enhanced stiffness without altering a functionality of the string (912). The hanging portion (19) of the string (912) has same thickness/diameter (24) as known string and is freely suspended in the vaginal cavity (18).

Figure 12:
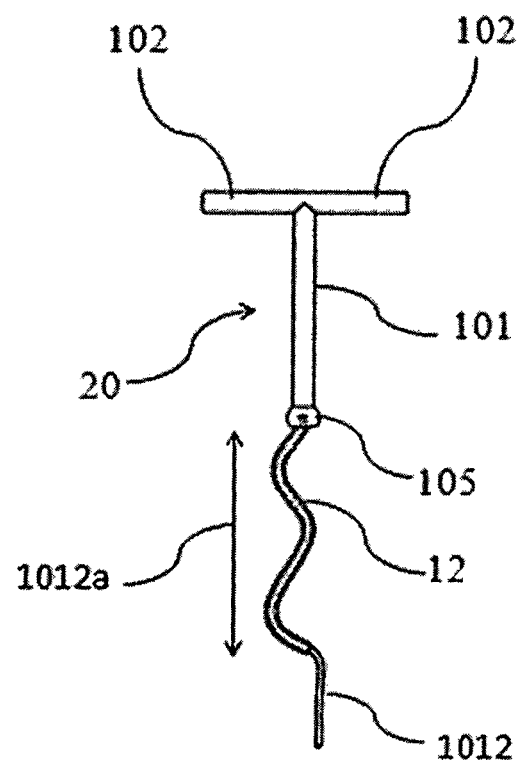
Figure 12A:
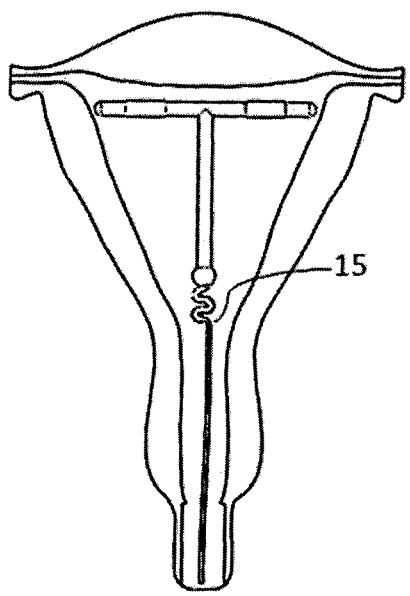
FIGS. 12A and 12B show the extent of envelope.
Figure 12B:
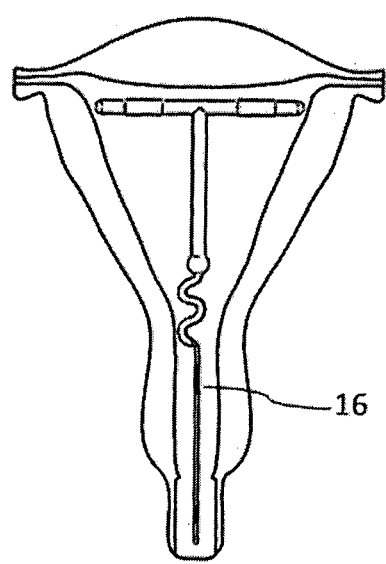

According to this invention, an enhanced stiffness is also achieved by providing an envelope around the string(s). FIG. 12 shows a preferred embodiment with an IUD (20) having one or more strings (1012) emerging from the spherical bulge (105) of IUD (20). The string(s) (1012) is guided by a tubular extension (12) of the spherical bulge (105) below the spherical bulge (105). The tubular extension (12) is straight or curvilinear. The tubular extension (12) is of such a length that the tubular extension (12) ends above the internal cervical os (15) as shown in FIG. 12A; or the tubular extension (12) is of such a length that the tubular extension (12) enters the endocervical canal (16) partially, as shown in Figure-12B. The length of said string(s) (1012) inside the tubular extension (12) forms the projected length (1012a) of the string(s) (1012). The tubular extension (12) provides the required stiffness without altering a functionality of the string. The tubular extension (12), when curvilinear, also provides a springy action during the contraction of the uterus, preventing the curling of the string(s) (1012) inside the uterus (17). The hanging portion (19) of said string(s) (1012) is freely suspended in the vaginal cavity (18).

Figure 13:
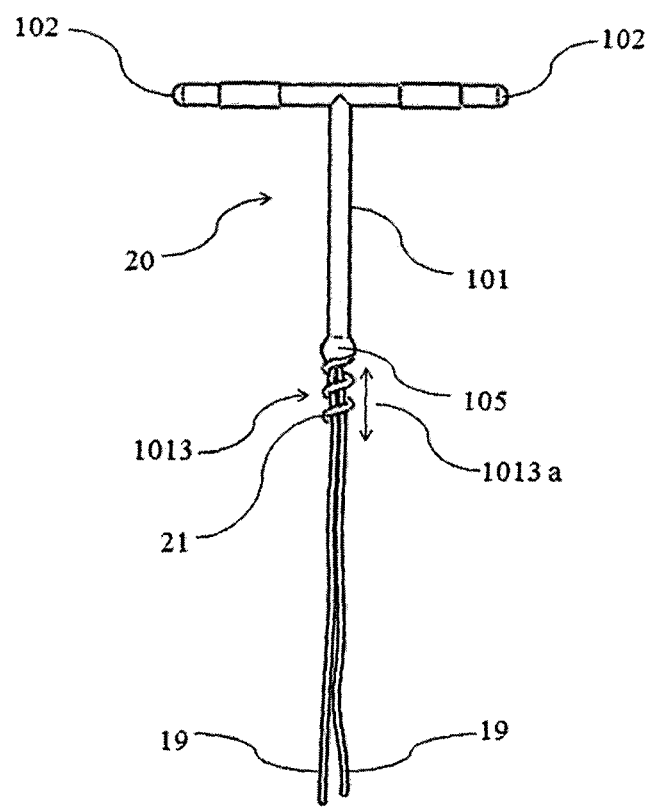
Figure 13A:
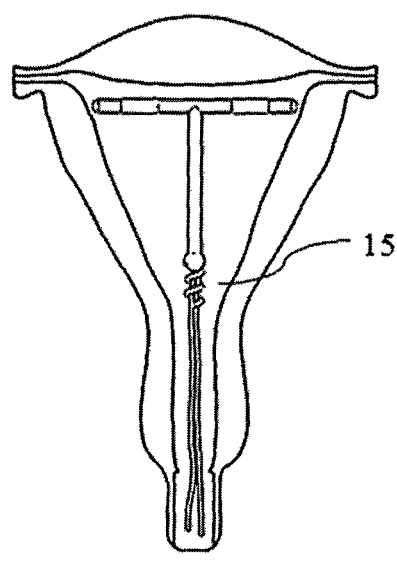
FIGS. 13A and 13B show the extent of envelope.
Figure 13B:
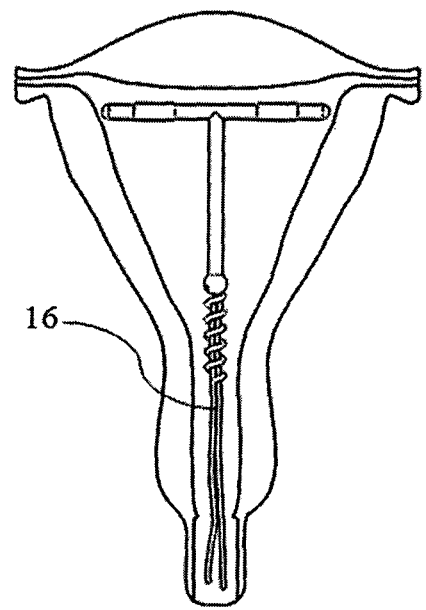

FIG. 13 shows another embodiment with an IUD (20) having one or more strings (1013) emerging from the spherical bulge (105) of IUD (20). The string(s) (1013) is fenced around, by a springy curvilinear extension (21) of the spherical bulge (105) below the spherical bulge (105). The springy curvilinear extension (21) is of such a length that the springy curvilinear extension (21) ends above the internal cervical os (15) as shown in FIG. 13A; or the springy curvilinear extension (21) is of such a length that the springy curvilinear extension (21) enters the endocervical canal (16) partially, as shown in FIG. 13B. The length of said string(s) (1013) inside the springy curvilinear extension (21) forms the projected length (1013a) of the string(s) (1013). The springy curvilinear extension (21) provides the enhanced stiffness without altering the functionality of the string. The springy curvilinear extension (21) also provides the springy action during the contraction of the uterus preventing the curling of the string(s) (1013) inside the uterus (17). The hanging portion (19) of said string(s) (1013) is freely suspended in the vaginal cavity (18).

Figure 14:
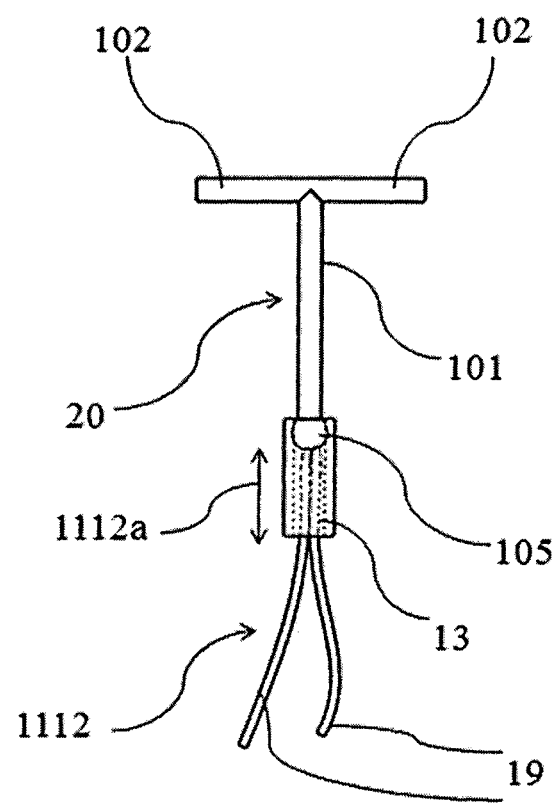
Figures 14A, 14B:
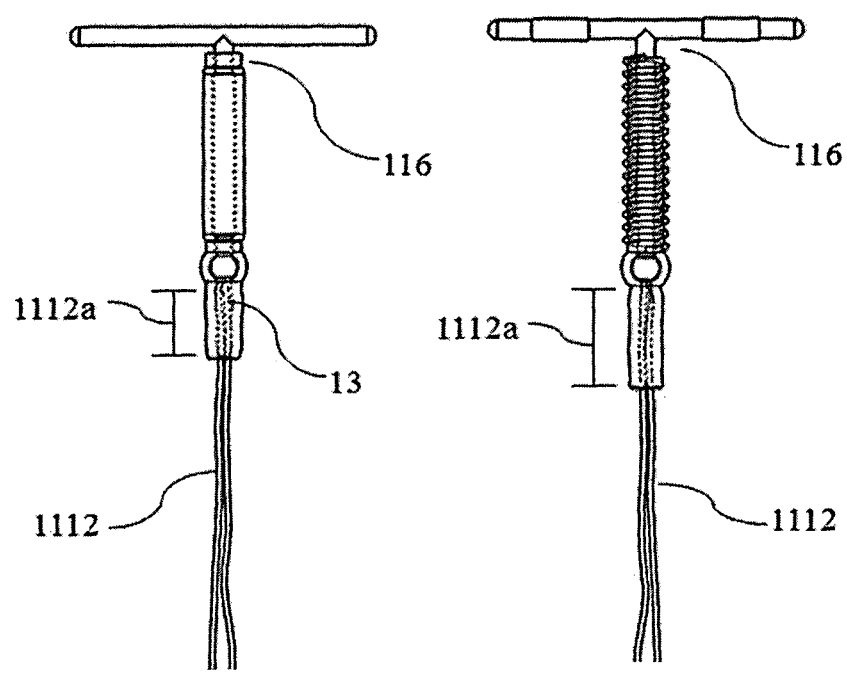
FIGS. 14A, 14B, 14C and 14D show the extent of envelope on either ends.
Figure 14C:
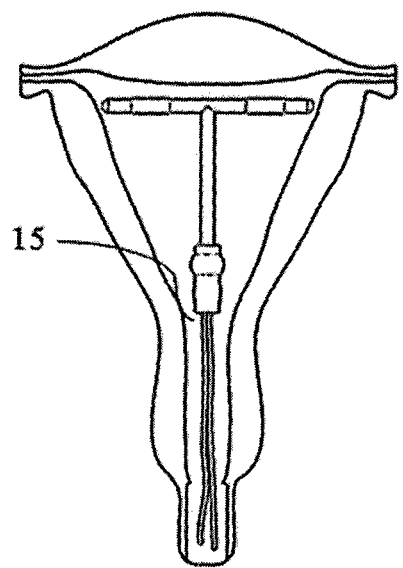
Figure 14D:
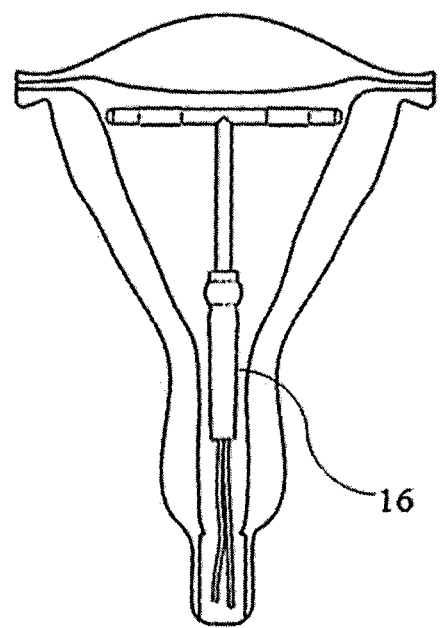

In another embodiment as shown in the FIG. 14, for an IUD (20) having one or more string (1112) emerging from the spherical bulge (105) of the IUD (20), the string(s) (1112) is guided by a stretchable hollow tube (13). The stretchable hollow tube (13) at least covers the spherical bulge (105) additionally. The hollow tube (13) may cover beyond the spherical bulge as shown in FIG. 14A towards the proximal end (116), by being above the previously present copper winding or drug chamber. The stretchable hollow tube (13) may also cover beyond spherical bulge as shown in FIG. 14B towards the proximal end (116), by being below the previously present copper winding or drug chamber. The length of stretchable hollow tube (13) towards the string(s) (1112) is such that the hollow tube (13) ends above the internal cervical os (15) as shown in FIG. 14C. The length of the hollow tube (13) towards the string(s) (1112) can also be such that the hollow tube (13) partially enters the endocervical canal (16) as shown in FIG. 14D. In all variations, the ends of the hollow tube are sealed in order to prevent harboring of infection. The length of said two or more/a single string (1112) inside the hollow tube (13) forms the projected length (1112a) of the strings (1112).The hollow tube (13) restricts the upward movement of said string(s) (1112) from curling up inside the uterus (17). The hanging portion (19) of said string(s) (1112) is freely suspended in the vaginal cavity (18).

Figure 15:
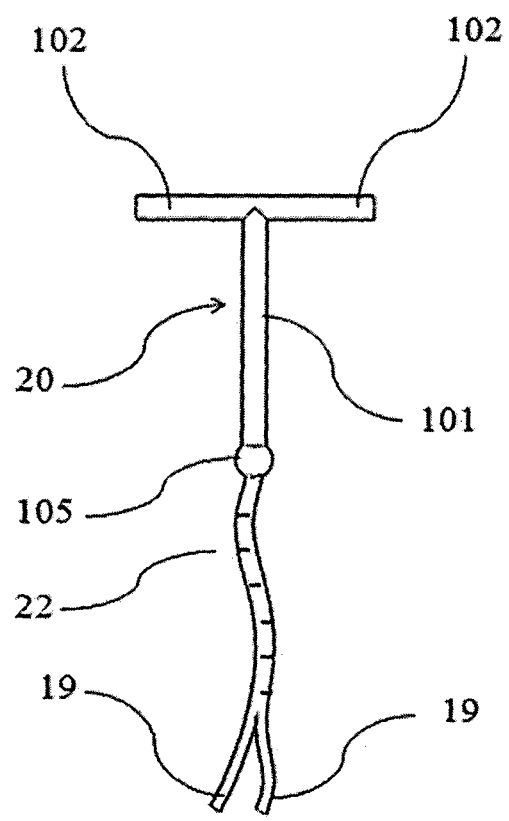
FIG. 15 shows identification marks provided on the string(s).

In all above embodiments, the string is optionally provided with a plurality of identification by way of a mark, as show in FIG. 15, whether formed during manufacturing of the string or subsequently by an additional process, at measured intervals. Such identification aids the surgeon in cutting a right length of the string or the filament after leaving a recommended length of string of about 2 to 3 cm in the vaginal cavity.

Figure 16:
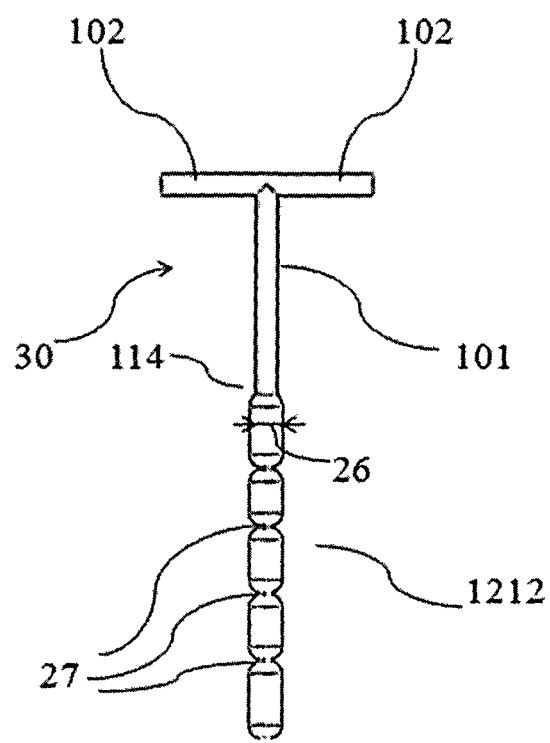
FIG. 16 shows a single string in the form of a filament with identification marks.

In yet another embodiment as shown in FIG. 16 a hormone-releasing intrauterine system, abbreviated as an IUS (30), as per this invention has a single string in the form of a filament (1212) of "jelly-like" extra soft material immediately below the distal end (114) of the stem (101). The diameter (26) of the filament is of the order of 1.5 to 10 times the diameter of a prior art string, with constrictions (27) at measured intervals. The constriction (27) facilitates trimming of the filament at desired measured length. The filament cannot curl up, and can cause no discomfort to the woman and or her partner.

The spherical bulge illustrative shown in the FIG. 16 is of a diameter more than a diameter of the central vertical stem, however, the spherical bulge can be of the diameter same as or less than the diameter of the central vertical stem.

We claim:

1. An intrauterine device with a restricted upward movement of a plurality of strings, having an elongated central vertical stem of an order of 29 to 35 mm in length with a plurality of arms attached on a proximal end of the central vertical stem and a spherical bulge attached on a distal end of the central vertical stem, wherein the plurality of strings are terminated together on one end at the spherical bulge, and each of the plurality of strings has an opposite, unterminated end that together form a hanging portion of said plurality of strings configured to suspend freely from the spherical bulge in the vaginal cavity, and an envelope directly connected to the spherical bulge by at least covering the spherical bulge and wherein the envelope has sealed ends to prevent harboring of infection, and wherein the envelope is disposed around the hanging portion of the plurality of strings emerging from below the spherical bulge to achieve an enhanced stiffness fora projected length of the hanging portion of plurality of strings proximal to the attachment to the spherical bulge, with the hanging portion of plurality of strings extending away from the spherical bulge and beyond said envelope without retention between the envelope and the unterminated ends of the hanging portion of strings, and configured to remain inside the endocervical canal so as to restrict the upward movement of the plurality of strings in the uterus.

2. The intrauterine device with the restricted movement of the plurality of strings as claimed in claim 1, wherein said envelope around the plurality of strings is a tubular extension of the spherical bulge.

3. The intrauterine device with the restricted movement of the plurality of strings as claimed in claim 2, wherein said tubular extension is curvilinear.

4. The intrauterine device with the restricted movement of the plurality of strings as claimed in claim 2, wherein said tubular extension is straight.

5. The intrauterine device with the restricted movement of the plurality of strings as claimed in claim 2, wherein said tubular extension is of such length that the tubular extension is configured to ends above the internal cervical os.

6. The intrauterine device with the restricted movement of the plurality of strings as claimed in claim 2, wherein said tubular extension is of such length that the tubular extension is configured to partially enters the endocervical canal.

7. The intrauterine device with the restricted movement of the plurality of strings as claimed in claim 1, wherein said envelope around the plurality of strings is a springy curvilinear extension of the spherical bulge and the plurality of strings is fenced around by the springy curvilinear extension.

8. The intrauterine device with the restricted movement of the plurality of strings as claimed in claim 7, wherein said springy curvilinear extension is of such a length that the springy curvilinear extension is configured to ends above the internal cervical OS.

9. The intrauterine device with then restricted movement of the plurality of strings as claimed in claim 7, wherein said springy curvilinear extension is of such a length that the springy curvilinear extension is configured to partially enters the endocervical canal.

10. The intrauterine device with the restricted movement of the plurality of strings as claimed in claim 1, wherein said envelope around the plurality of strings is a stretchable hollow tube of the spherical bulge and the plurality of strings is guided by the stretchable hollow tube.

11. The intrauterine device with the restricted movement of the plurality of strings as claimed in claim 10, wherein said stretchable hollow tube at least covers the spherical bulge.

12. The intrauterine device with then restricted movement of the plurality of strings as claimed in claim 10, wherein said stretchable hollow tube covers beyond the spherical bulge towards the proximal end having a copper winding or a drug chamber.

13. The intrauterine device with then restricted movement of the plurality of strings as claimed in claim 10, said stretchable hollow tube is of such a length that the stretchable hollow tube is configured to ends above the internal cervical os.

14. The intrauterine device with then restricted movement of the plurality of strings as claimed in claim 10, said stretchable hollow tube is of such a length that the stretchable hollow tube is configured to partially enters the endocervical canal.

\* \* \* \* \*